(12) United States Patent
Rojas-Pardini

(10) Patent No.: US 7,625,206 B2
(45) Date of Patent: Dec. 1, 2009

(54) METHOD OF ORTHODONTIC TREATMENT

(76) Inventor: Pablo Rojas-Pardini, P.O. Box 2664 9A, Panama (PA)

( * ) Notice: Subject to any disclaimer, the term of this patent is extended or adjusted under 35 U.S.C. 154(b) by 0 days.

(21) Appl. No.: 11/145,376

(22) Filed: Jun. 3, 2005

(65) Prior Publication Data

US 2008/0160475 A1 Jul. 3, 2008

Related U.S. Application Data

(60) Provisional application No. 60/576,524, filed on Jun. 3, 2004.

(51) Int. Cl.
*A61C 3/00* (2006.01)
(52) U.S. Cl. .................. 433/24; 433/8; 433/9
(58) Field of Classification Search ............... 433/24, 433/8, 18, 20, 22, 9
See application file for complete search history.

(56) References Cited

U.S. PATENT DOCUMENTS

| | | | |
|---|---|---|---|
| 3,091,856 A * | 6/1963 | Goldstein | 433/18 |
| 4,037,324 A | 7/1977 | Andreasen | |
| 4,880,380 A * | 11/1989 | Martz | 433/11 |
| 5,018,969 A | 5/1991 | Andreiko et al. | |
| 5,039,303 A * | 8/1991 | Irwin | 433/24 |
| 2003/0203333 A1* | 10/2003 | Vallittu et al. | 433/20 |
| 2004/0157184 A1* | 8/2004 | Reising | 433/8 |

FOREIGN PATENT DOCUMENTS

WO WO2008/053269 * 5/2008

OTHER PUBLICATIONS

Angle, Edward H., "The Angle system of regulation and retention of the teeth, and treatment of fractures of the maxillae", 1897, S.S. White Dental MFG. Co.: Philadephia, 5th Ed., pp. 28-48.*

* cited by examiner

*Primary Examiner*—Jonathan S. Werner
*Assistant Examiner*—Michael R Ballinger
(74) *Attorney, Agent, or Firm*—Allen, Dyer, Doppelt, Milbrath & Gilchrist, P.A.

(57) ABSTRACT

A method of orthodontic treatment includes fastening a first bracket to an inside surface of a first tooth in a patient's mouth, fastening a second bracket to an outside surface of a second tooth, the second tooth being adjacent the first tooth, fastening a third bracket to an outside surface of a third tooth, the third tooth being adjacent the first tooth and generally opposite the second tooth, passing a wire between the first and second teeth, positioning the wire around the first tooth adjacent the inside surface and the first bracket, passing the wire between the first and third teeth, and connecting the wire to the first, second and third brackets.

29 Claims, 5 Drawing Sheets

METHOD OF ORTHODONTIC TREATMENT

RELATED APPLICATION

This application claims priority from co-pending provisional application Ser. No. 60/576,524, which was filed on Jun. 3, 2004, and which is incorporated herein by reference in its entirety.

FIELD OF THE INVENTION

The present invention relates to the field of dental medicine and, more particularly, to a method of orthodontic treatment.

BACKGROUND OF THE INVENTION

Orthodontia is that branch of dental medicine which is concerned with correcting abnormally aligned or positioned teeth. Typical orthodontic treatment involves fastening small brackets to the surface of the teeth and connecting these brackets with a wire which can be tightened so as to exert a pulling force on the teeth through the brackets. The pulling force gradually urges the teeth to shift position within the patient's mouth. Brackets have traditionally been placed on the outside surfaces of the teeth, that is, on surfaces which face away from the patient's tongue; these surfaces which are also termed labial surfaces.

Because brackets and orthodontic wires are usually silver-colored appliances, they give the orthodontic patient a look which children have unkindly labeled "metal mouth." Partly for that reason, alternatives have been sought that would lessen the metal mouth appearance of the patient.

One such alternative has been the placement of the brackets on the inner surfaces of the teeth, that is, those surfaces which face toward the patient's tongue, also called lingual surfaces. This results in the orthodontic appliance being worn on the inside of the teeth, so that the patient's outward appearance is substantially normal. Having the orthodontic apparatus along the inside of the teeth, however, is uncomfortable and some patients never quite become accustomed to this mode of treatment.

A second alternative has been the use of enamel-colored plastic brackets and wire of a color which blends in with the patient's natural tooth enamel. These plastic devices are usually positioned along the outer, labial surfaces of the teeth.

Nevertheless, standard orthodontic treatment has relied on positioning of the brackets along the same set of surfaces on the teeth being treated. That is, the brackets are all positioned along outer surfaces, or are all positioned along inner surfaces of the teeth.

Regardless of positioning of the brackets in these standard approaches, the duration of treatment can be quite lengthy for properly repositioning the patient's teeth. Furthermore, because the brackets are usually glued onto the teeth, brackets sometimes detach from teeth which are being urged to move by pull exerted by the wire on the bracket.

SUMMARY OF THE INVENTION

With the foregoing in mind, the present invention advantageously provides an orthodontic treatment method which shortens the treatment period by urging teeth under treatment to move faster and which decreases the likelihood that the bracket will detach from a tooth being repositoned.

Standard orthodontic techniques used in cases of light to moderate crowding and non-extraction cases typically employ pressure applied to the teeth without having first created space into which the teeth should move. The presently described method, called the interproximal threading or weaving procedure, makes treatment more effective, as it helps open space first and then moves the teeth into the created space. Additionally, the present procedure applies biomechanical principles in creating tension in the interproximal area by a connector, typically a wire, weaved or passed around the tooth to be moved, thereby simultaneously creating mesiodistal space and moving the tooth.

Accordingly, the invention provides a method of orthodontic treatment. In an exemplary embodiment, the method comprises fastening a first bracket to an inside surface of a first tooth in a patient's mouth. A second bracket is fastened to an outside surface of a second tooth, the second tooth being adjacent the first tooth. A third bracket is fastened to an outside surface of a third tooth, the third tooth being adjacent the first tooth and generally opposite the second tooth. A wire is passed between the first and second teeth and is looped around the inside surface of the first tooth so that it is adjacent the first bracket. The wire is also passed between the first and third teeth. Finally, the wire is connected to the first, second and third brackets.

It should be understood that in the present invention the term "tooth" is employed to indicate any of the teeth in a patient's mouth, including incisors (the front teeth), cuspids (sometimes also known as "canines"), bicuspids (sometimes also known as "premolars") and molars. Additionally, these teeth may be lowers, that is, part of the mandibular dentition, or uppers, that is, part of the maxillary dentition.

BRIEF DESCRIPTION OF THE DRAWINGS

Some of the features, advantages, and benefits of the present invention having been stated, others will become apparent as the description proceeds when taken in conjunction with the accompanying drawings, presented solely for exemplary purposes and not with intent to limit the invention thereto, and in which.

DETAILED DESCRIPTION OF THE PREFERRED EMBODIMENT

Figures 1A, 1B:
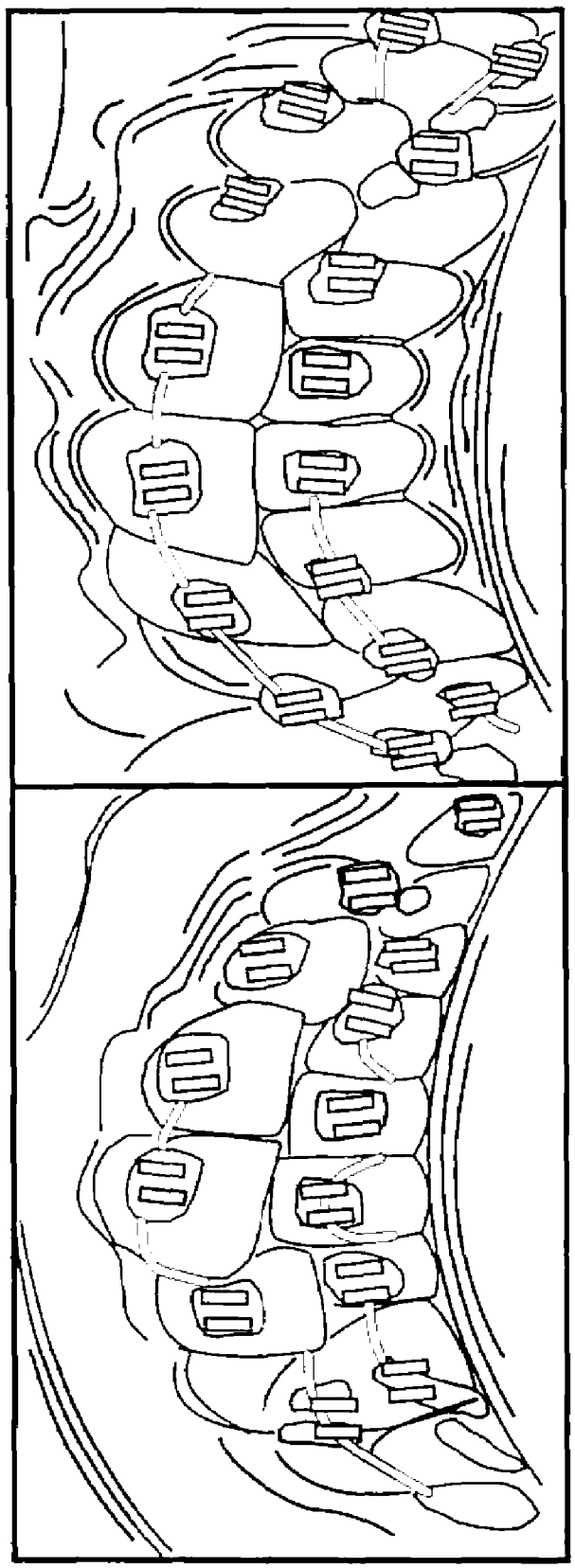
FIG. 1 is a front perspective view of a patient being treated with the orthodontic treatment method according to an embodiment of the present invention, wherein 1A is a view earlier in the treatment and 1B is a view later in the treatment.

The present invention will now be described more fully hereinafter with reference to the accompanying drawings, in which preferred embodiments of the invention are shown. Unless otherwise defined, technical and scientific terms used herein have the same meaning as commonly understood by one of ordinary skill in the art to which this invention pertains.

Although methods and materials similar or equivalent to those described herein can be used in the practice or testing of the present invention, suitable methods and materials are described below. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided solely for exemplary purposes so that this disclosure will be thorough and complete, and will fully convey the scope of the invention to those skilled in the art. Other features and advantages of the invention will be apparent from the following detailed description, and from the claims.

FIGS. 1-5 illustrate various aspects of the present method of orthodontic treatment. In contrast to standard orthodontic treatment where brackets are placed all on generally the same side of the teeth being treated, in the present invention at least one bracket is positioned on a tooth surface along an opposite side of the tooth from the placement of the remaining brackets. This approach is illustrated in FIGS. 1 through 4.

The present orthodontic treatment method is also called the interproximal threading (or weaving) procedure and, typically, employs a wire as the connector used between brackets. An orthodontic wire which is useful in this method is Nitinol® brand in 0.012 XL or 0.014 XL gauges, by Unitek Corporation of Monrovia, Calif., and particularly when it is weaved in an open finger spring shape. Regarding the present invention, some of the applicable medical terminology is explained below, although not all these terms are otherwise used in this application.

Interproximal, refers to the space between the lateral surfaces of adjoining teeth.

Mesial, identifies an aspect of each tooth which is toward the center or midline of the patient's head.

Distal, is generally the opposite of mesial, that is, an aspect of a tooth which is positioned away from the center or midline of the patient's head.

Contact point, generally means the contact surface between adjacent teeth.

The dental papilla is a somewhat triangular gingival portion between adjacent teeth.

Tension results from tightening the wire connector between brackets and results in a force being applied by the wire to a tooth under treatment.

Lingual describes an aspect of a tooth which is oriented toward the patient's tongue.

Labial describes an aspect of a tooth which is oriented away from the patient's tongue and toward the lips or cheeks.

Interdental indicates between one tooth and another.

Posterior teeth are those located toward the back of the oral cavity, including bicuspids and molars.

Anterior teeth are those located toward the entrance of the oral cavity, including incisors and canines, also known as cuspids.

Superior arch refers to the upper teeth, that is, the maxillary dentition.

Inferior arch refers to the lower teeth, that is, the mandibular dentition.

Nitinol® is the brand name of a preferred orthodontic wire for use in the present invention and which can recover its form after being deformed.

Figures 2A, 2B, 2C:
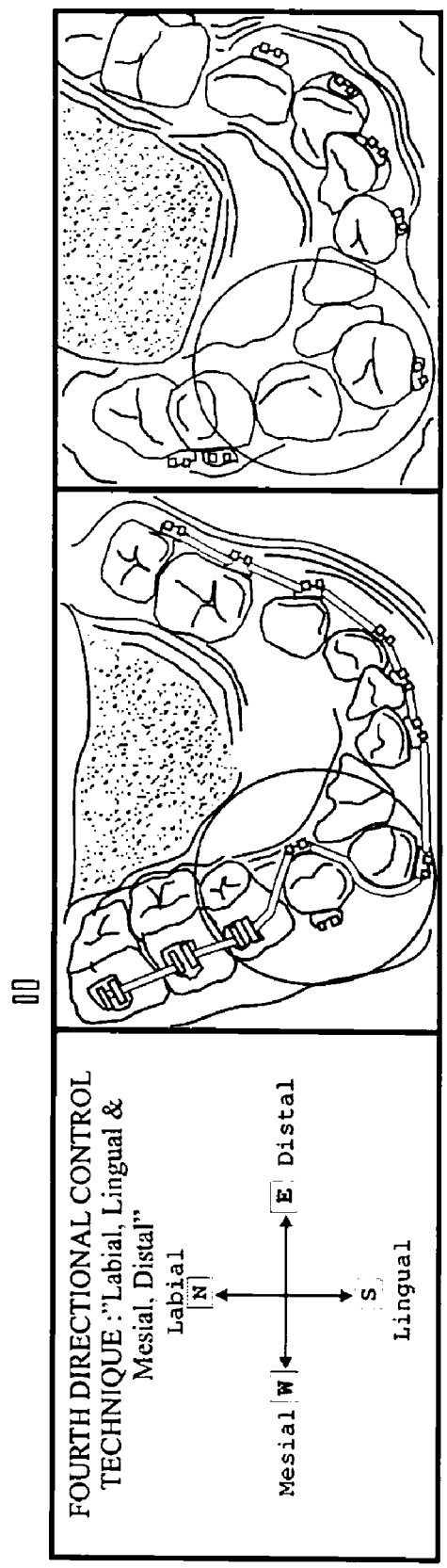
FIG. 2 shows a top view of a patient's inferior arch being treated according to the present method, wherein panel 2A shows the various directional controls available through the method, 2B shows the patient earlier in treatment and 2C shows the patient later in treatment.

Accordingly, for example, the present invention provides a method of orthodontic treatment which includes fastening a first bracket to an inside surface, a lingual surface, of a first tooth in a patient's mouth. As known to those skilled in the art, positioning a bracket on a tooth, or fastening a bracket, comprises firmly attaching the bracket to the tooth, typically but not exclusively by means of an adhesive composition which bonds the bracket onto the tooth surface. The method also calls for fastening a second bracket to an outside surface, a labial surface, of a second tooth, the second tooth being adjacent the first tooth. The method continues by fastening a third bracket to an outside or labial surface of a third tooth, the third tooth being adjacent the first tooth and generally opposite the second tooth. The method includes passing (also threading or weaving) a wire between the first and second teeth, placing the wire around the inside (lingual) surface of the first tooth and the first bracket, and passing the wire between the first and third teeth. Passing the wire between teeth causes the opening of a space between the teeth being treated and prepares the orthodontic appliance for then connecting the wire to the first, second and third brackets. It should be understood, however, that the method of the present invention does not require that the steps be implemented in the order described. This embodiment of the invention is shown in FIG. 2, which additionally shows in panel 2B a tooth under treatment having an unused bracket positioned on the outside surface of the tooth, a bicuspid (circled), so that the tooth has brackets on both an inside and an outside surface. This additional bracket is useful at a point in the treatment where it may be desirable to alter the directional force applied to the tooth by rerouting the wire from the inside bracket to the outside bracket. As depicted in panel 2A of the same figure, the directional forces may be applied to a tooth in any one of four directions, labial, lingual, mesial, distal, and combinations thereof. Panel 2C shows the same patient when further along in treatment at a time when the wire has been temporarily removed and consideration is being given to redirecting the forces acting on the teeth being treated.

Figures 3A, 3B, 3C:
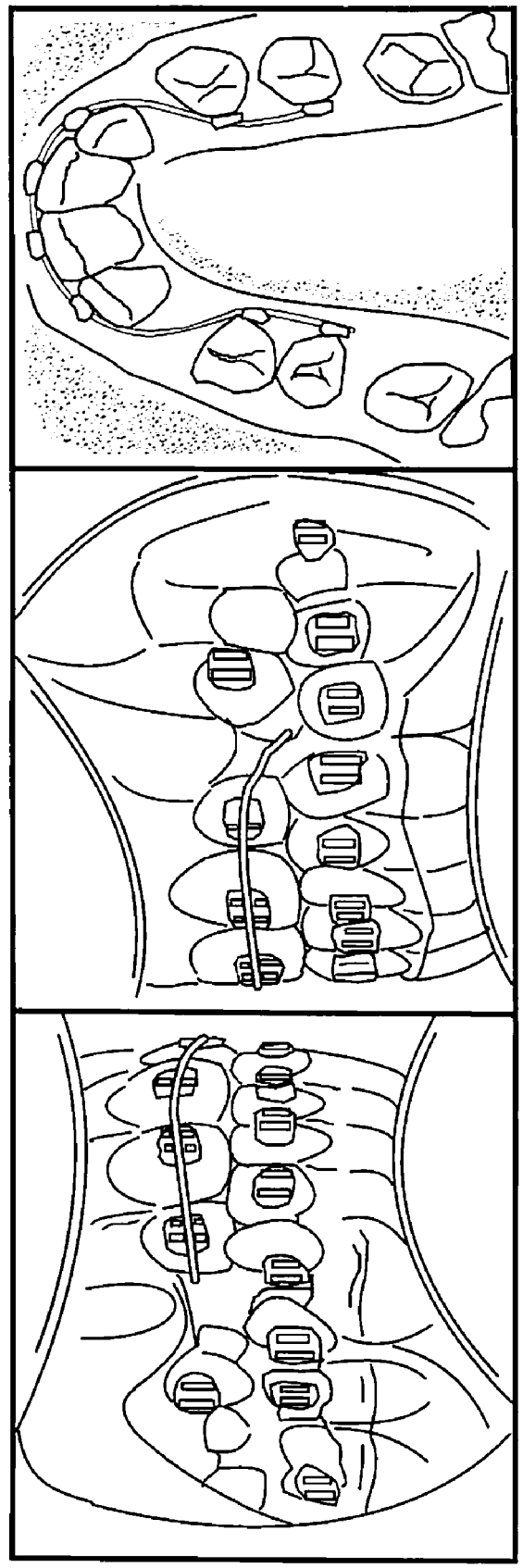
FIG. 3 shows a left view (3A), a right view (3B) and a plan view of the superior arch (3C) of a patient under treatment with the present method.

Another, slightly different embodiment of the invention is a method of repositioning a tooth within a patient's mouth. An example is shown in FIG. 3. The method comprises selecting at least a first tooth to be repositioned and having at least second and third teeth adjacent thereto on generally opposite sides of the first tooth, an arrangement best seen in panel FIG. 3C. FIGS. 3A and 3B are right and left views of the same patient. Brackets are positioned on the first, second and third teeth, wherein a bracket on the first tooth is positioned on a lingual surface of the tooth and wherein brackets on the second and third teeth are positioned on labial surfaces of the teeth. The method then calls for passing a wire between the first and second teeth and between the first and third teeth so that a portion of the wire extends along the lingual surface of the first tooth adjacent the first bracket and portions of the wire lie adjacent the brackets on the labial surfaces of the second and third teeth. Finally, the method includes connecting the wire to the brackets on the first, second and third teeth.

Yet another embodiment of the invention is a method of orthodontic treatment comprising positioning a first bracket on a surface of a first tooth in a patient's mouth, positioning a second bracket on a surface of a second tooth adjacent the first tooth, wherein the second bracket is positioned on the second tooth generally opposite from the position of the first bracket on the first tooth, and positioning a third bracket on a surface of a third tooth adjacent the first tooth on a side generally opposite from the second tooth, and wherein the third bracket is positioned on the third tooth generally opposite from the position of the first bracket on the first tooth. Connecting a wire to the first, second and third brackets so as to exert tension between at least two of the brackets ends this method.

Figure 4C:
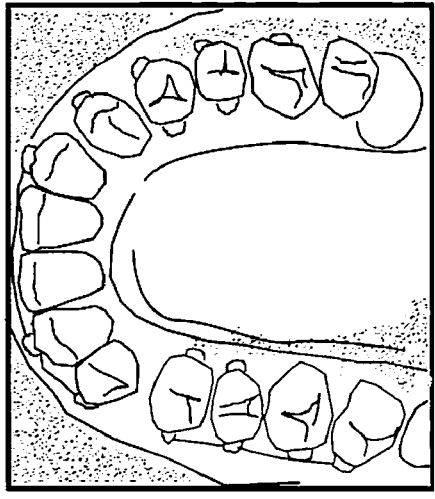
FIG. 4 shows various plan views of a patient being treated by the present method, wherein 4A-C are views of the superior arch and 4D-E are views of the inferior arch.
Figure 4B:
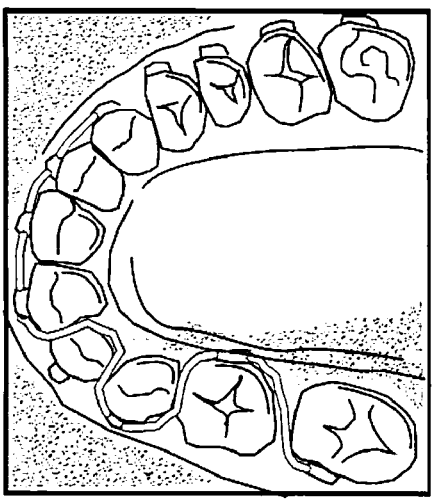
Figure 4A:
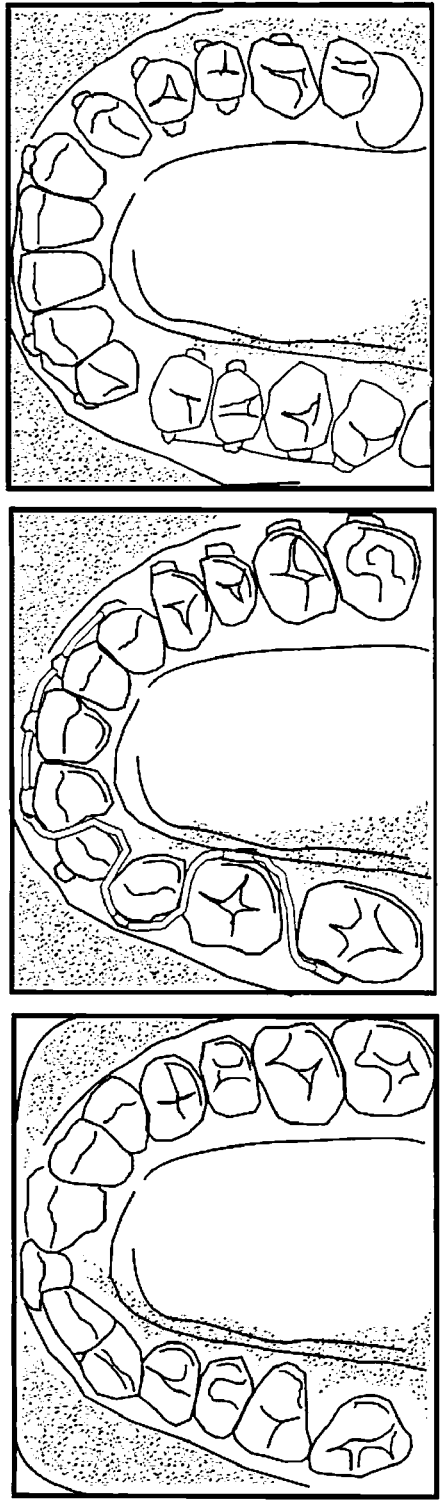
Figure 4E:
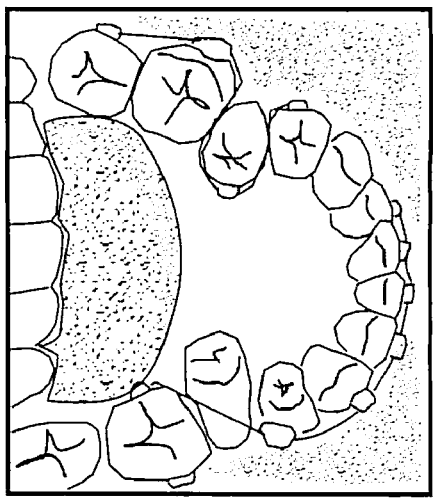
Figure 4D:
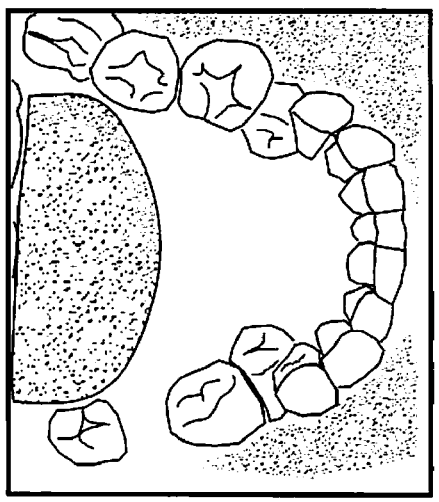

Lastly, the invention also includes a method of orthodontic treatment comprising establishing a first point of connection on a surface of a first tooth in a patient's mouth, establishing a second point of connection on a surface of a second tooth adjacent the first tooth, wherein the second point of connection is positioned on the second tooth generally opposite from the position of the first point of connection on the first tooth and establishing a third point of connection on a surface of a third tooth adjacent the first tooth, wherein the third point of connection is positioned on the third tooth generally opposite from the position of the first point of connection on the first tooth. Finally, the method includes connecting together the first, second and third points of connection. FIG. 4 shows the superior arch (4A-C) and inferior arch (4D-E) of a patient under treatment with such a method, the points of connection being the typical brackets in this case, although the method includes any other effective point of connection. FIG. 4A shows the patient's superior arch before treatment; FIG. 4B shows the superior arch during treatment; and FIG. 4C shows the superior arch with treatment almost completed. FIG. 4D shows the inferior arch before treatment and being treated in FIG. 4E.

Figure 5C:
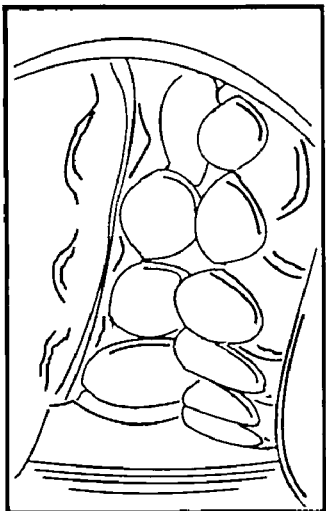
FIG. 5 shows before and after photos of a patient treated by the present method, where 5A-C are right, front and left views before treatment and where 5D-F are right, front and left views after treatment.
Figure 5B:
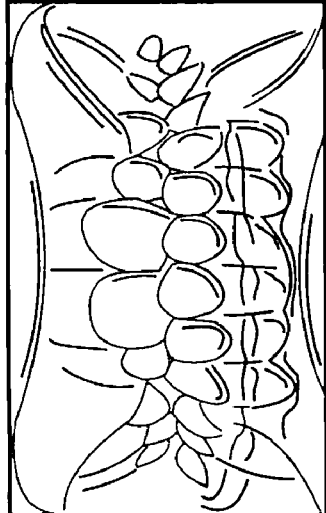
Figure 5A:
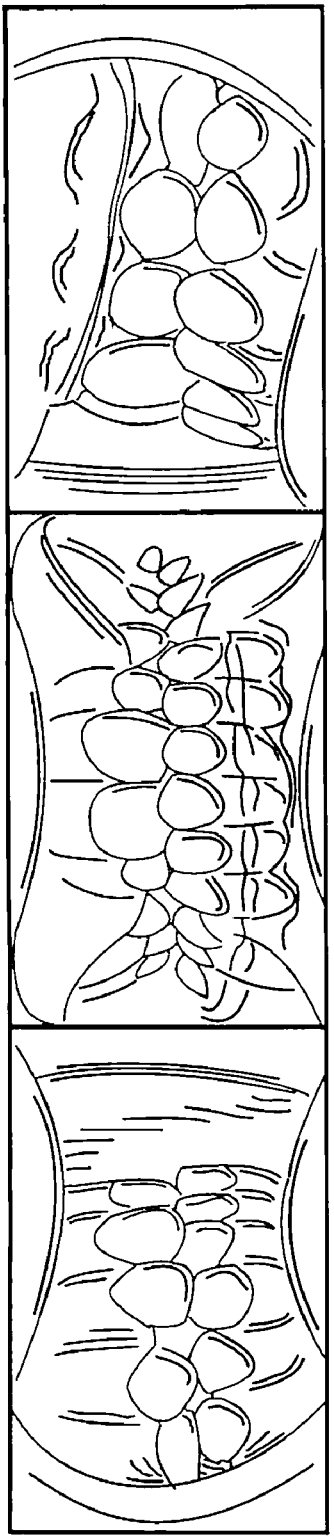
Figure 5F:
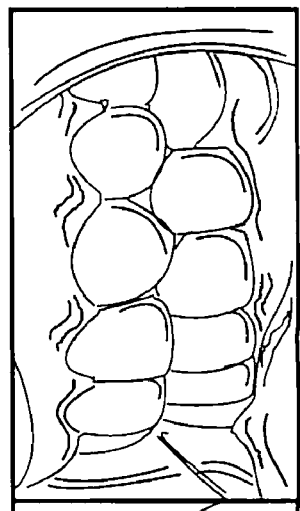
Figure 5E:
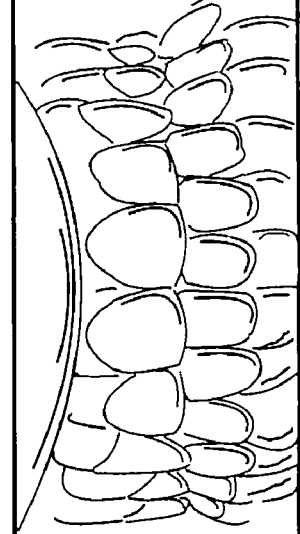
Figure 5D:
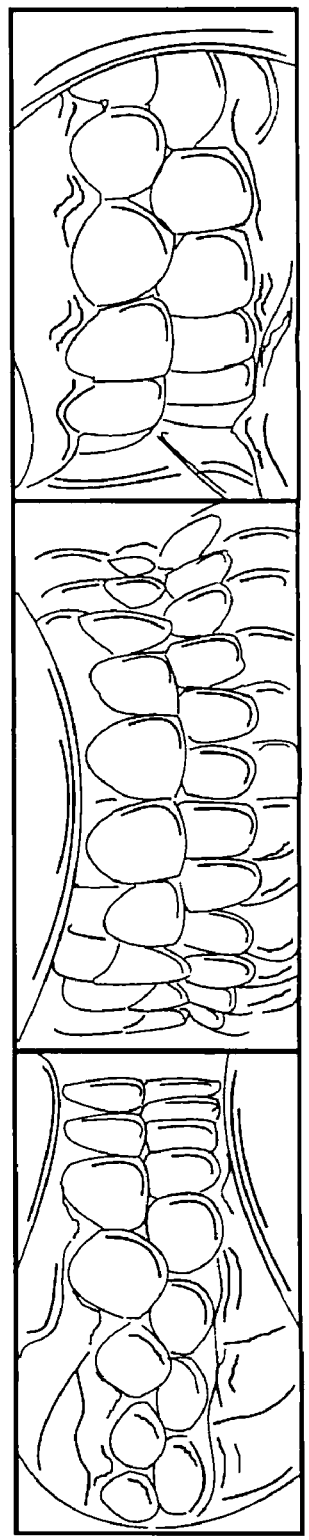

The inventive method of treatment disclosed herein provides at least two advantages over previously known orthodontic treatments. First, by placing a point of connection, typically a bracket, on the side of a tooth opposite from where the brackets are positioned on adjacent teeth and then connecting these brackets together, the force applied to the one tooth changes from a pulling force, which is exerted in the usual treatment, to a pushing force due angle of the wire relative to the tooth. This principle is illustrated in FIG. 2, panel 2B. Second, as also shown in panel 2B, passing the wire between teeth helps push the adjoining teeth slightly apart and creates space between the teeth. While not wishing to be bound to any specific theory of the invention's operation, the inventor believes the combination of changing the angle of the force acting on the tooth under treatment and creating space between teeth helps the teeth move faster with this treatment than with conventional orthodontic treatment. FIGS. 5A-C show left, frontal and right views of a patient before treatment and FIGS. 5D-E show left, frontal and right views of the same person following treatment.

Additional aspects of the present method of orthodontic treatment include adjusting the connection, or tightening, of the wire to at least one of the second and third brackets so as to cause the wire to apply a force to the first bracket. The method may also include forming one or more loops in the wire between brackets, or forming one or more angles in the wire between brackets.

As noted above, it should be understood that the terms "tooth" or "teeth" are used herein in a generic sense to include incisors, cuspids, bicuspids, and molars. Also, the tooth or teeth may be selected from lower teeth or from upper teeth.

Accordingly, in the drawings and specification there have been disclosed typical preferred embodiments of the invention and, although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as recited in the appended claims.

That which is claimed:

1. A method of professional orthodontic treatment, the method comprising:
    bonding a first bracket to a labial surface of a first tooth in a patient's mouth;
    bonding a second bracket to a lingual surface of a second tooth, the second tooth being a tooth to be repositioned;
    bonding a third bracket to a labial surface of a third tooth, the third tooth being next to the second tooth, the second tooth being a middle tooth between the first tooth and the third tooth;
    passing an orthodontic wire between the first and second teeth;
    looping the wire around the lingual surface of the second tooth;
    passing the wire between the second and third teeth; and
    connecting the wire to the first, second and third brackets.

2. The method of claim 1, further comprising adjusting the connection of the wire to at least one of the first and third brackets so as to cause the wire to apply a force to at least the second bracket.

3. The method of claim 1, wherein connecting further comprises tightening the wire between at least the first and third brackets.

4. The method of claim 1, further comprising adjusting the connection of the wire to at least one bracket so as to cause the wire to apply a force to another bracket.

5. The method of claim 1, further comprising one or more loops formed in the wire between brackets.

6. The method of claim 1, further comprising one or more angles formed in the wire between brackets.

7. The method of claim 1, wherein at least one of the first, second and third teeth is selected from an incisor, a cuspid, a bicuspid, and a molar.

8. The method of claim 1, wherein the first, second and third teeth are selected from lower arch teeth.

9. The method of claim 1, wherein the first, second and third teeth are selected from upper arch teeth.

10. A method for an orthodontist to reposition a tooth within a patient's mouth, the method comprising:
    selecting at least one first tooth to be repositioned, said at least one first tooth being positioned between second and third teeth;
    bonding brackets on the at least one first tooth, and the second and third teeth, wherein a first bracket on the at least one first tooth is fastened on a labial surface of the tooth and wherein brackets on the second and third teeth are fastened on lingual surfaces of the teeth;
    passing an orthodontic wire between the at least one first tooth and the second tooth and between the at least one first tooth and the third tooth so that a portion of the wire abuts the first bracket and so that the wire extends to the brackets on the labial surfaces of the second and third teeth; and
    connecting the wire to all the brackets.

11. The method of claim 10, further comprising tightening the wire between the connections to at least two brackets.

12. The method of claim 10, further comprising adjusting the connection of the wire to brackets on at least the second and third teeth so as to cause the wire to apply a force to the bracket on the first tooth.

13. The method of claim 10, wherein connecting further comprises tightening the wire between at least brackets on the second and third teeth.

14. The method of claim 10, further comprising adjusting the connection of the wire to at least one bracket so as to cause the wire to apply a force to another bracket.

15. The method of claim 10, further comprising one or more loops formed in the wire between brackets.

16. The method of claim 10, further comprising one or more angles formed in the wire between brackets.

17. The method of claim 10, wherein at least one of the first, second and third teeth is selected from an incisor, a cuspid, a bicuspid, and a molar.

18. The method of claim 10, wherein the first, second and third teeth are selected from lower arch teeth.

19. The method of claim 10, wherein the first, second and third teeth are selected from upper arch teeth.

20. A method of professional orthodontic treatment comprising:
- bonding a first bracket on a surface of a first tooth in a patient's mouth, the surface selected from a labial surface and a lingual surface;
- bonding a second bracket on a surface of a second tooth next to the first tooth, said second bracket being bonded to a lingual surface of the second tooth if said first bracket was bonded to a labial surface of the first tooth and being bonded to a labial surface of the second tooth if said first bracket was bonded to a lingual surface of the first tooth;
- bonding a third bracket on a labial or lingual surface of a third tooth the second and third teeth having the first tooth between them, said third bracket being bonded to a lingual surface of the third tooth if said first bracket was bonded to a labial surface of the first tooth and being bonded to a labial surface of the third tooth if said first bracket was bonded to a lingual surface of the first tooth; and
- connecting an orthodontic form-recovering wire to the first, second and third brackets so as to exert tension in the wire between at least two of the brackets.

21. The method of claim 20, further comprising adjusting the connection of the wire to at least one of the second and third brackets so as to cause the wire to apply a force to the first bracket.

22. The method of claim 20, wherein connecting further comprises tightening the wire between at least the second and third brackets.

23. The method of claim 20, further comprising adjusting the connection of the wire to at least one bracket so as to cause the wire to apply a force to another bracket.

24. The method of claim 20, further comprising one or more loops formed in the wire between brackets.

25. The method of claim 20, further comprising one or more angles formed in the wire between brackets.

26. The method of claim 20, wherein at least one of the first, second and third teeth is selected from an incisor, a cuspid, a bicuspid, and a molar.

27. The method of claim 20, wherein the first, second and third teeth are selected from lower arch teeth.

28. The method of claim 20, wherein the first, second and third teeth are selected from upper arch teeth.

29. A method of professional orthodontic treatment comprising:
- establishing a first point of connection on a surface of a first tooth in a patient's mouth, said first tooth surface having a first orientation selected from labial or lingual;
- establishing a second point of connection on a surface of a second tooth next to the first tooth, wherein the second tooth surface is selected from labial or lingual but opposite form the orientation of the first tooth surface;
- establishing a third point of connection on a surface of a third tooth, the second and third teeth having the first tooth between them, wherein the third tooth surface is selected from labial or lingual but opposite from the orientation of the first tooth surface; and
- connecting together the first, second and third points of connection with an orthodontic form-recovering wire, wherein connecting comprises one or more loops formed in the wire between points of connection.

* * * * *